(12) United States Patent
Slade et al.

(10) Patent No.: US 10,449,061 B2
(45) Date of Patent: Oct. 22, 2019

(54) INSTRUMENT FOR MANIPULATING AN IMPLANT

(71) Applicant: Biomet UK Healthcare Limited, Bridgend (GB)

(72) Inventors: Jonathan James Slade, South Wales (GB); Robert John Andrew Bigsby, South Wales (GB)

(73) Assignee: Biomet UK Healthcare Limited (GB)

( * ) Notice: Subject to any disclaimer, the term of this patent is extended or adjusted under 35 U.S.C. 154(b) by 156 days.

(21) Appl. No.: 15/110,505

(22) PCT Filed: Jan. 7, 2015

(86) PCT No.: PCT/GB2015/050011
§ 371 (c)(1),
(2) Date: Jul. 8, 2016

(87) PCT Pub. No.: WO2015/104537
PCT Pub. Date: Jul. 16, 2015

(65) Prior Publication Data
US 2016/0331551 A1    Nov. 17, 2016

(30) Foreign Application Priority Data
Jan. 10, 2014  (GB) .................................. 1400430.3

(51) Int. Cl.
*A61F 2/46* (2006.01)
*A61B 17/92* (2006.01)
*A61F 2/30* (2006.01)

(52) U.S. Cl.
CPC ............ *A61F 2/4607* (2013.01); *A61B 17/92* (2013.01); *A61F 2/4609* (2013.01);
(Continued)

(58) Field of Classification Search
CPC .................................................... A61F 2/4609
(Continued)

(56) References Cited

U.S. PATENT DOCUMENTS

| 5,540,697 A | * | 7/1996 | Rehmann | A61F 2/4609 294/95 |
|---|---|---|---|---|
| 2010/0249857 A1 | | 9/2010 | Chana et al. | |
| 2012/0053592 A1 | * | 3/2012 | Burgi | A61F 2/4609 606/91 |

FOREIGN PATENT DOCUMENTS

| EP | 2572679 A1 | 3/2013 |
|---|---|---|
| EP | 3091943 B1 | 11/2018 |

(Continued)

OTHER PUBLICATIONS

"Applicattion Serial No. 15700776.6, Response filed Apr. 3, 2017 to Office Action dated Sep. 30, 2016", 21 pgs.
(Continued)

*Primary Examiner* — Matthew J Lawson
(74) *Attorney, Agent, or Firm* — Schwegman Lundberg & Woessner, P.A.

(57) ABSTRACT

An instrument (10) for manipulating a prosthetic implant (2) the instrument comprising: an attachment element (20), operable to engage the Implant; an actuation rod (SO), a distal end (50a) of which is connected to the attachment element; and a stem (14), the actuation rod being at least partially moveably received within the stem, wherein the attachment element is bendable between a first position in which the attachment element does not engage the implant and a second position in which the attachment element engages the Implant, the actuation rod being configured so as to selectively bend the attachment element between the first and second positions upon movement of the actuation rod.

20 Claims, 6 Drawing Sheets

(52) U.S. Cl.
 CPC ............ *A61F 2002/30484* (2013.01); *A61F 2002/30565* (2013.01); *A61F 2002/4623* (2013.01); *A61F 2002/4627* (2013.01); *A61F 2002/4628* (2013.01)

(58) Field of Classification Search
 USPC .......................................... 606/91
 See application file for complete search history.

(56) References Cited

FOREIGN PATENT DOCUMENTS

| | | |
|---|---|---|
| FR | 2830746 A1 | 4/2003 |
| GB | 2445087 A | 6/2008 |
| WO | WO-2008099242 A1 | 8/2008 |
| WO | WO-2015104537 A1 | 7/2015 |

OTHER PUBLICATIONS

"International Application Serial No. PCT/GB2015/050011, International Preliminary Report on Patentability dated Jul. 21, 2016", 8 pgs.
"International Application Serial No. PCT/GB2015/050011, International Search Report dated Apr. 1, 2015", 6 pgs.
"International Application Serial No. PCT/GB2015/050011, Written Opinion dated Apr. 1, 2015", 6 pgs.

\* cited by examiner

INSTRUMENT FOR MANIPULATING AN IMPLANT

CLAIM OF PRIORITY

This application is a U.S. National Stage Filing under 35 U.S.C. 371 from International Application No. PCT/GB2015/050011 filed on Jan. 7, 2015, and published as WO 2015/104537 A1 on Jul. 16, 2015, which claims the benefit of United Kingdom Application No. 1400430.3 filed on Jan. 10, 2014, the benefit of priority of each of which is claimed hereby, and each of which are incorporated by reference herein in its entirety.

The present invention relates to an instrument for manipulating an implant, and particularly, but not exclusively, relates to an instrument for handling and impaction of a joint prosthesis component, such as an acetabular cup.

BACKGROUND

During a joint replacement procedure, it is necessary to manipulate prosthesis components into their required positions with respect to patient anatomy. In the case for example of a hip replacement prosthesis, it is necessary to manoeuvre an acetabular cup into a prepared patient acetabulum, and it may also be necessary to impact the cup into the prepared recess. It is known to use specific tools for the manipulation and impaction of prosthesis components in this manner.

In order to allow a gripping or impaction tool to gain purchase on an implant, it is usual for the implant to include one or more attachment features onto which the gripping and/or impaction tool can engage in order to manipulate the implant. This is particularly the case with acetabular cups, which do not otherwise lend themselves to easy engagement with a gripping or impaction tool. Typical attachment features for an acetabular cup might include a threaded apical bore, operable to receive a threaded rod, as well as projecting lugs and undercuts, all designed to engage with corresponding attachment features on a gripping and/or impaction instrument. This arrangement works well for multiple body acetabular cups, which comprise an external shell and separate internal bearing component. In this type of construction the external shell may be provided with any appropriate attachment features for interaction with a gripping or impaction tool. Once in place, these attachment features are completely covered by the separate bearing component that is fitted into the cuter shell.

Attachment to a gripping or impaction tool becomes more problematic when considering single body, or so called Monobloc acetabular cups. This type of implant component comprises a single body having an outer bone engaging surface and an inner bearing surface. In such a component, the capacity to accommodate additional attachment features is severely limited. The internal bearing surface must remain free of any surface discontinuities or other aberrations and thus is not available for the provision of attachment features. Even temporary attachment mechanisms have proven extremely difficult to implement. The condition of the bearing surface is vital to the success and longevity of the implant. Thus, any temporary attachment procedure must be carefully controlled to ensure that no possibility of damage to the highly polished bearing surface can arise.

An additional issue that must be considered within the context of implant manipulation is the release of the implant from the relevant tool once the implant is in position. The implant may be considerably less accessible once in position, and removal or release from a tool may involve gaining direct access to the implant through the wound incision. Such direct contact is undesirable and carries risks of additional accidental contact with the implant and consequent damage to the bearing surface.

SUMMARY OF THE INVENTION

According to a first aspect of the present invention there is provided an instrument for manipulating a prosthetic implant, the instrument comprising: an attachment element, operable to engage the implant; wherein the attachment element is bendable between a first position in which the attachment element does not engage the implant and a second position in which the attachment element engages the implant; and an actuator, the actuator being configured so as to selectively bend the attachment element between the first and second positions upon actuation of the actuator.

The actuator may on rise an actuation rod. A distal end of the actuation rod may be connected to the attachment element. The actuation rod may be configured so as to selectively bend the attachment element between the first and second positions upon movement of the actuation rod. The instrument may further comprise a stem. The actuation rod may be at least partially moveably received within the stem.

The attachment element and actuation rod may be configured such that rotation of the actuation rod causes the attachment element to bend between the first position and the second position. Alternatively or additionally, the attachment element and actuation rod may be configured such that linear movement of the actuation rod causes the attachment element to bend between the first position and the second position.

The attachment element may comprise an opening for receiving the actuation rod. The opening may be provided at a centre of the attachment element. The opening may be threaded for receiving a threaded portion of the actuation rod. By virtue of the threaded opening and actuation rod, rotation of the actuation rod may cause linear movement of the attachment element opening, thereby bending the attachment element between the first and second positions.

The attachment element may be constrained from rotating with respect to the remainder of the instrument.

The attachment element may grip a rim of the implant. The attachment element may be configured to selectively grip a rim of the implant. The attachment element may grip at two or more points on the rim, for example the attachment element may grip rim at three or four points on the rim.

The attachment element may be symmetrical. For example, the attachment element may possess rotational symmetry about a longitudinal axis of the actuation rod. The attachment element may be, cross shaped, e.g. cruciform.

The attachment element may comprise one or more pivot surfaces or edges. The pivot surfaces or edges may be configured to interact with a corresponding surface or edge of the instrument (e.g. a surface or edge of the impaction member mentioned below) so as to form a pivot about which a portion of the attachment element may rotate when the attachment element bends between the first and second positions.

The attachment element may comprise one or more arms extending from a hub, e.g. in a substantially radial plane. The arms may be configured to flex with respect to the hub. The hub may comprise the attachment element opening. Each arm may comprise the pivot surface or edge. The arm pivot surface or edge may be provided at a point towards a distal end (e.g. radially outermost end) of the arm. The arm pivot surface or edge may be set back from the distal end of the arm. The arm pivot surface or edge may comprise a rounded profile.

Each arm may comprise an engaging portion configured to engage the implant. The engaging portion may be provided at the distal end of the arms. The engaging portion and pivot surface or edge may be provided on opposite sides of the arm. The portion of the attachment element that may rotate when the attachment element bends between the first and second positions may comprise the engaging portion of the arm.

Each arm may comprise a reduced thickness portion. The reduced thickness portion may be configured to aid bending of the arm. The reduced thickness portion may provided between the distal end of the arm and the hub of the attachment element. In particular, the reduced thickness portion may be provided between the pivot surface or edge of the arm and the hub of the attachment element.

The instrument may further or comprise an impaction member. The impaction member may be provided at a distal end of the instrument, e.g., a distal end of the stem. The impaction member may be removably mounted, e.g. at the distal end of the instrument.

The impaction member may comprise an impaction surface, operable to engage a corresponding, e.g. annular, surface of the implant. The impaction surface may be at least partially annular.

The impaction member may comprise one or more centring formations configured to centre the impaction member with respect to the implant. The impaction member may comprise one or more channels. The or each channel may be configured to receive a respective arm of the attachment element. The centring formations may be provided between the channels.

The impact on member may be formed from a polymer material.

The impaction member may comprise one or more pivot surfaces or edges. The impaction member pivot surfaces or edges may be configured to interact with a corresponding surface or edge of the attachment element so as to form a pivot about which a portion of the attachment element rotates when the attachment element bends between the first and second positions. The impaction member pivot surfaces or edges may comprise a substantially flat or a rounded profile.

The impaction member and the remainder of the instrument, e.g. the stem, may comprise cooperating formations operable to prevent relative rotation between the impaction member and the remainder of the instrument. The impaction member may comprise formations operable to prevent relative rotation between the impaction member and the attachment element.

The instrument may comprise are activation device operable to actuate the actuator. The activation device may drive relative movement between the actuation rod end the remainder of the instrument, e.g. the stem. The activation device may be mounted on the stem. The activation device may rotate with respect to the stem. The activation device may comprise a push button or a lever or any other device for activating the actuator.

The instrument may be for gripping and in action of the implant.

A kit of parts may comprise the above-mentioned instrument. The kit of parts may further comprise a plurality of impaction members. The impaction members be configured for a range of implants. The kit of parts may further comprise a plurality a attachment elements. The attachment elements may be configured for a range of implants.

According to a second aspect of the present in here is provided a method of manipulating a prosthetic implant the method comprising: providing an instrument comprising: an attachment element and an actuator, the method further comprising actuating the actuator so as to selectively bend the attachment element between a first position in which the attachment element does not engage the implant and a second position in which the attachment element engages the implant.

BRIEF DESCRIPTION OF THE DRAWINGS

For a better understanding of the present invention, and to show more clearly how it may be carried into effect, reference will now be made, by way of example, to the following drawings in which.

DETAILED DESCRIPTION OF EMBODIMENTS

Figure 1:
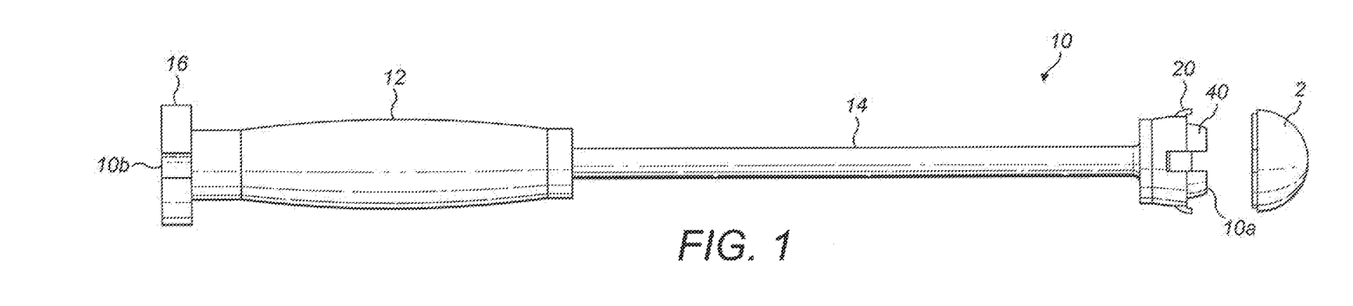
FIG. 1 is a side view of an impaction tool according to an example of the present invention and a corresponding acetabular cup implant.

With reference to FIG. 1 the present invention relates to an instrument, such as an impaction tool 10, for manipulating a prosthetic implant, such as an acetabular cup 2, The impaction tool 10 comprises an attachment element 20 provided at a distal end 10*a* of the impaction tool, An impaction member 40 may also be provided at the distal end 10*a* of the impaction tool handle 12 is provided at a proximal end 10*b* of the impaction tool. The handle 12 may comprise a surface that may be readily gripped by an operator of the instrument. A stem 14 is provided between the distal and proximal ends 10*a*, 10*b*. The handle 12 may be provided on, e.g. around, the stem 14 or the handle 12 may be a separate component, which connects to the stem 14.

As will be described in further detail below, the attachment element 20 is operable to selectively connect the distal end 10*a* of the impaction tool 10 to the acetabular cup 2. The attachment element 20 is movable from a first disengaged position to a second engaged position, in which the attachment element engages the acetabular cup 2. The attachment element 20 is activated via an activation device 16, which may be provided at the proximal end 10*b* of the impaction tool. The activation device 16 may be rotatable with respect to the stem 14, e.g. about a longitudinal axis of the impaction tool. The activation device 16 may be rotatably connected to the handle 12 and/or stem 14.

Figure 2:
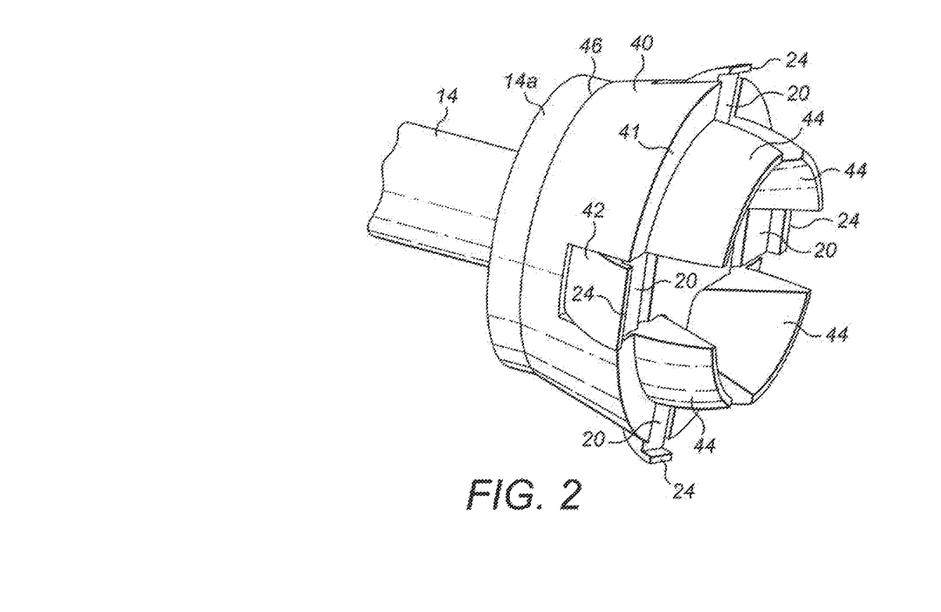
FIG. 2 is a perspective view of a distal end of the impaction tool according to the example of the present invention.

Referring to FIG. 2, the attachment element 20 and impaction member 40 are shown in more detail. The attachment element 20 comprises one or more arms 22 and in the particular example shown, four arms are provided. The arms 22 may extend substantially radially from the longitudinal axis of the impaction tool 10. For example, the arms 22 may extend in a substantially radial plane with respect to the longitudinal axis of the impaction tool 10; however, the arms may also extend in a direction with an axial component.

The attachment element arms 22 each comprise an engaging portion 24 configured to engage the acetabular cup 2. The engaging portions 24 are provided at a distal end, e.g. the radially outermost end, of the arms 22. The engaging portions 24 may extend in a substantially axial direction relative to the longitudinal axis of the impaction tool 10, at least when the attachment element 20 is in the disengaged position. By contrast, when the attachment element 20 is in the engaged position, the engaging portions 24 may extend with a radially inward component so as to grip the acetabular cup 2.

The impaction member 40 receives they attachment element 20. Accordingly, the impaction member 40 comprises one or more corresponding channels 42, which receive the attachment element arms 22, in the particular exam pie shown, four channels 42 are provided, one for each of the arms 22. It will be appreciated that relative rotation between the impaction member 40 and the attachment element 20 is prevented thanks to the placement of the attachment element arms 22 in the impaction member channels 42.

The impaction member 40 also comprises one or more centring formations 44 configured to centre the impaction member with respect to the acetabular cup. The centring formations 44 are provided between the channels 42 and as such, in the particular example shown, there are four centring formations 44. The centring formations 44 protrude from the distal end of the impaction tool. The centring formations 24 are shaped, e.g. curved, to correspond in shape to an inner surface, such as a bearing surface 4, of the acetabular cup 2.

The impaction member 40 also comprises an impaction surface 41 configured to abut a rim 6 of the acetabular cup 2. Accordingly, the impaction surface 41 may be circumferentially disposed out a longitudinal axis of the impaction member 40. The impaction surface 41 may be interrupted by the channels 42. The centring formations 44 may be radially set back from an edge of the impaction member 40, thereby forming the impaction surface 41. The attachment element arms 22 may be axially set back from the impaction surface 41 so that the arms 22 may not contact the rim 6 other than at the engaging portions 24.

The impaction member 40 may be formed from a scratch resistant material, such as a polymer, so that the impaction member does not scratch the bearing surface 4 of the acetabular cup 2. Furthermore, the impaction member 40 and/or attachment element 20 may be configured so that the attachment element 20, which may be formed from a metal, may not contact the bearing surface 4 of the acetabular cup 2. This may be achieved by one or more of the channels 42 being sufficiently deep to accommodate the attachment element arms 22, the provision of the centring formations 44 and the shape of the attachment element 20.

Figure 3A:
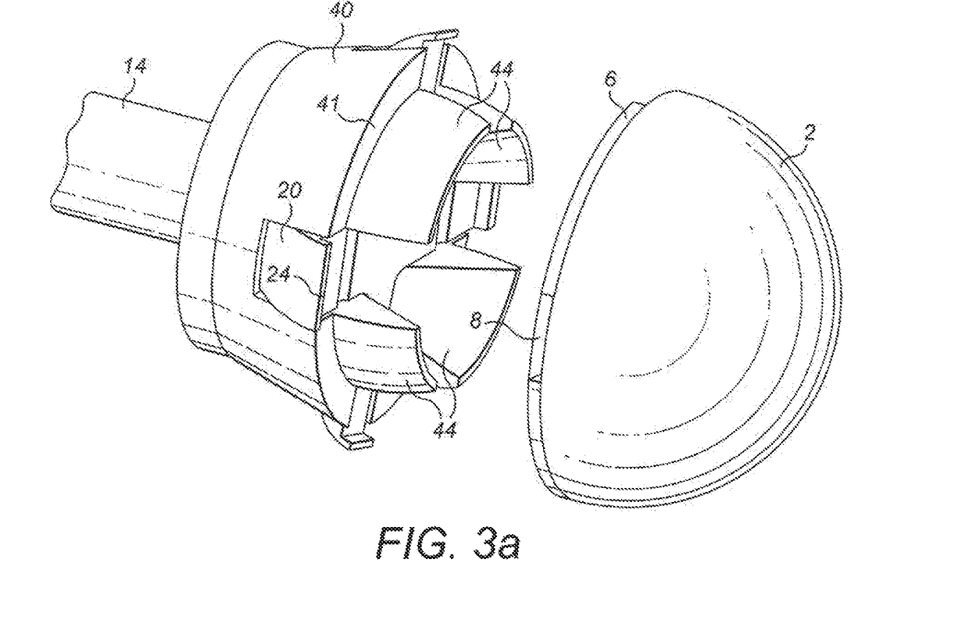
FIGS. 3*a* and 3*b* show the distal end of the impaction tool according to the example of the present invention before and after engagement with the acetabular cup respectively.
Figure 3B:
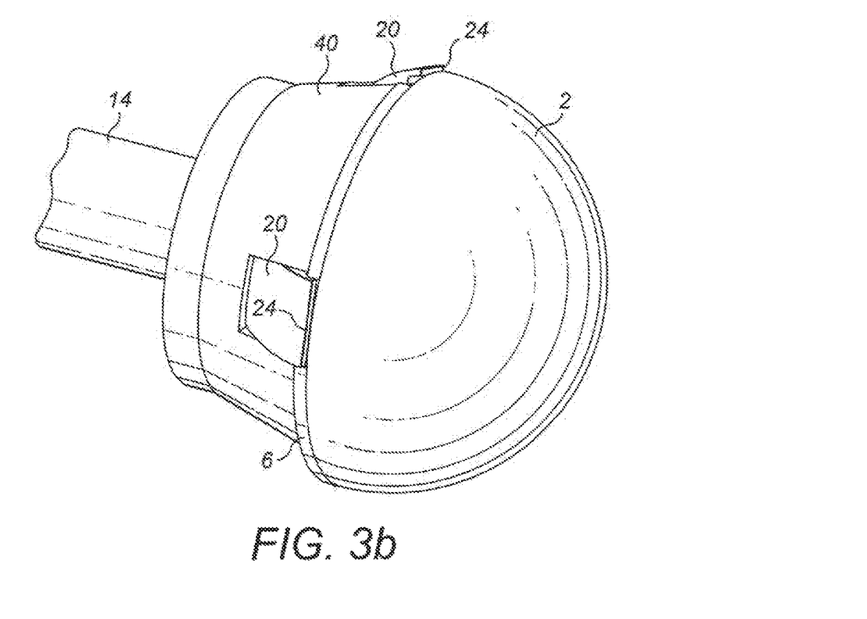

FIGS. 3a and 3b show the distal end of the impaction tool 10 before and after engagement with the acetabular cup 2 respectively. Accordingly, FIGS. 3a and 3b show the attachment element 20 in the disengaged position and engaged position respectively. As is depicted, the engaging portions 24 of the attachment element 20 may selectively engage the rim 6 of the acetabular cup. For example, the arm engaging portions 24 may selectively engage corresponding recesses 8 provided in the rim 6 of the acetabular cup 2. The recesses 8 may be provided on a radially outer facing surface of the rim 6. The number of recesses may correspond to the number of arms 22 and hence engaging portions 24, or there may be more recesses than arms.

In a particular example, there may be four equiangularly distributed rim recesses 8, one for each attachment element arm 22. The rim recesses 8 may be wedge shaped, for example with the rim recess radial thickness being thicker closer to the impaction tool 10. The provision of the recesses may rotatably lock the impaction tool to the acetabular cup 2.

Figure 8A:
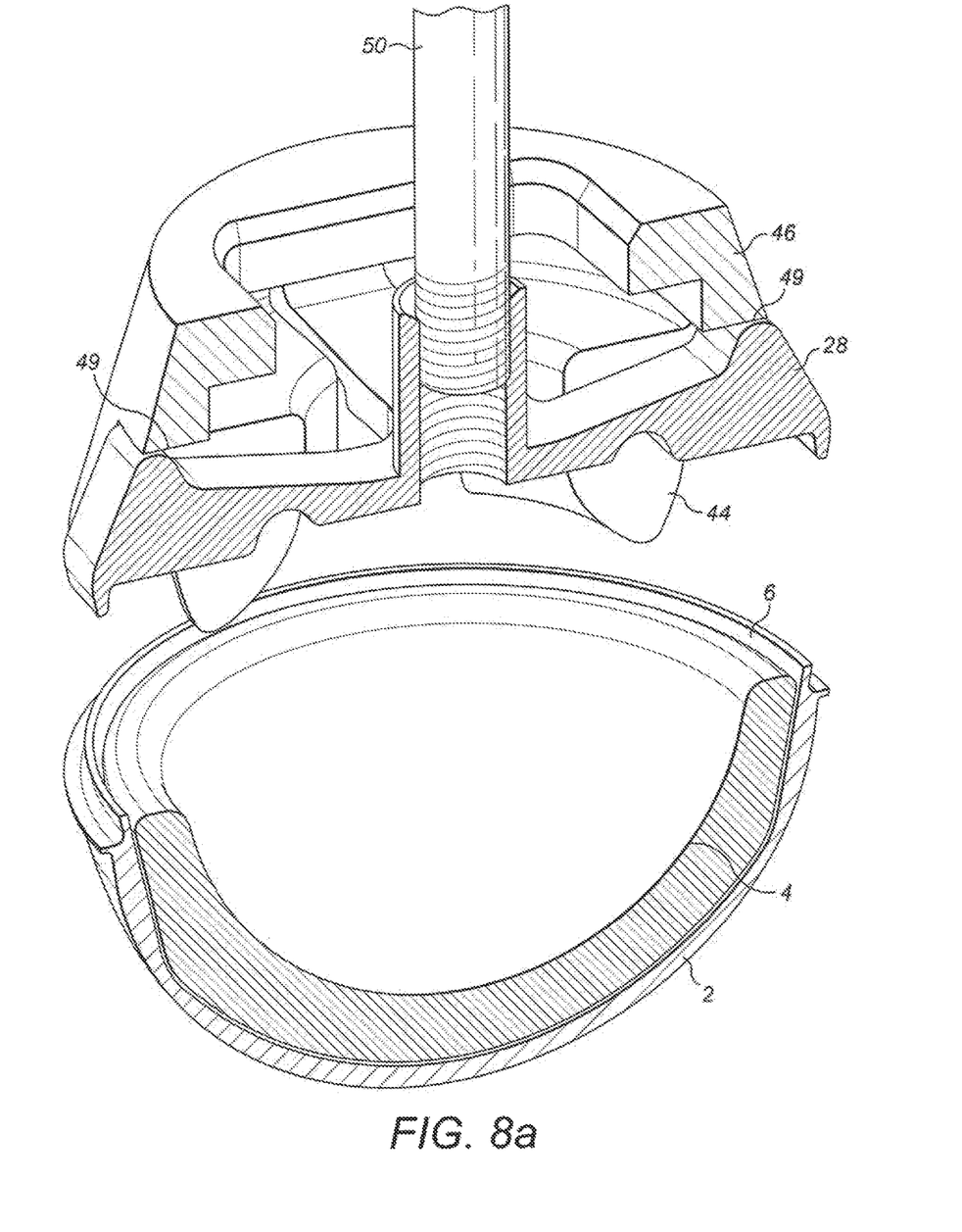
FIGS. 8*a* and 8*b* are perspective sectional views of the distal end of the impaction tool according to the example of the present invention before and after engagement with the acetabular cup respectively.
Figure 8B:
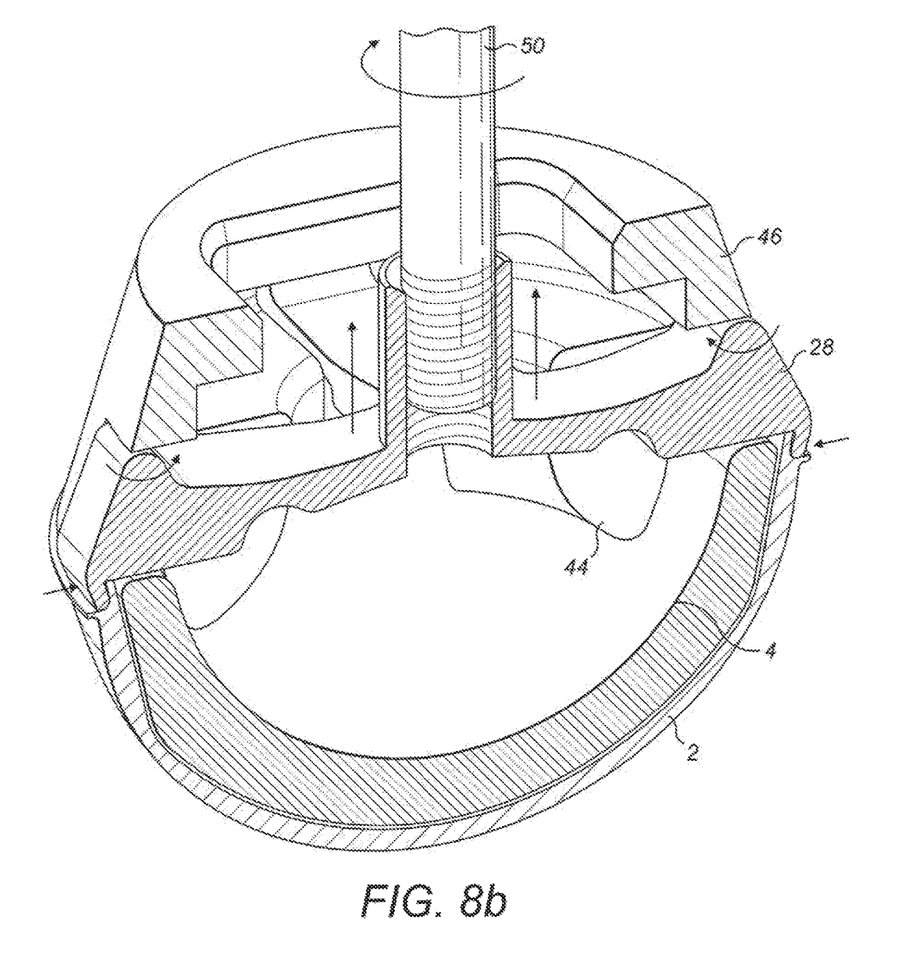

Alternatively, instead of having discrete rim recesses, the entire rim 6 may be shaped for the attachment element arms 22 to engage. Accordingly, there may be no recesses in the rim 6 (see for example FIG. 8) and the rim may instead be shaped for locking engagement with the arm engaging portions 24. For example, a radial outer wall of the rim 6 may be tapered, e.g. with an outer diameter of the rim at an edge of the rim facing the impaction tool 10 being greater than the outer diameter of the rim where the rim meets the remainder of the acetabular cup 2. In a further example, the radially outer facing surface of the rim 6 may be wedge shaped with the rim radial thickness being thicker closer to the impaction tool 10.

Figure 4:
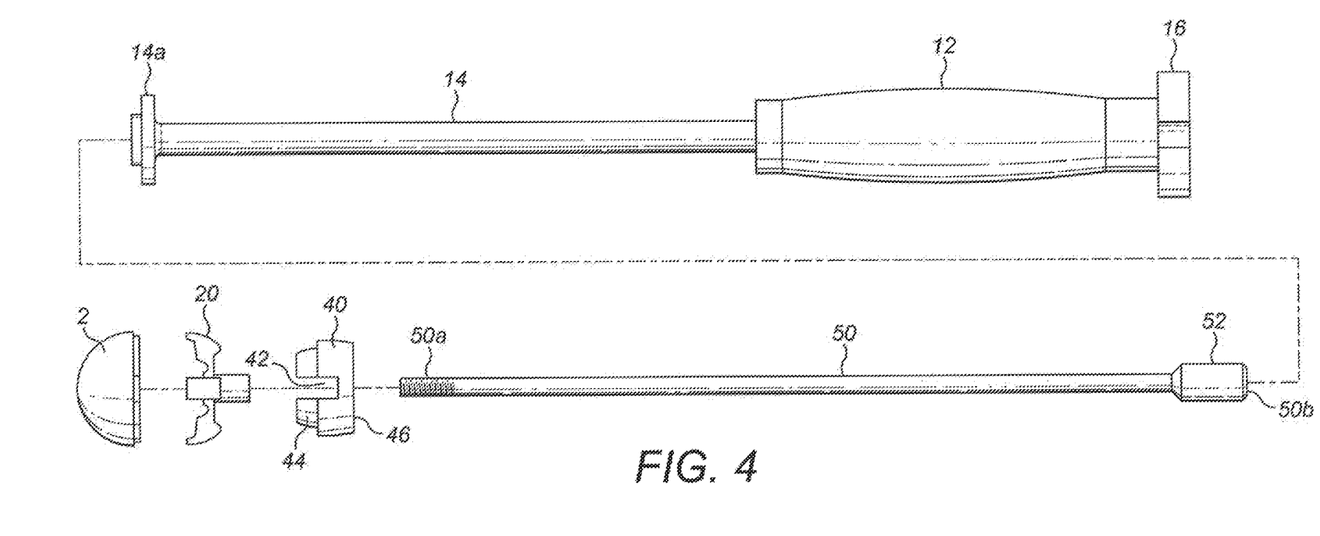
FIG. 4 is an exploded view of the impaction tool according to the example of the present invention.

FIG. 4 shows an exploded view of the impaction tool 10 according to the example of the present invention. As is depicted, the impaction tool 10 further comprises an actuator, such as an actuation rod 50. The actuation rod extends through a hollow in the handle 12, stem 14 and impaction member 40. A distal end 50a of the actuation rod 50 is connectable to the attachment element 20. The distal end 50a of the actuation rod 50 may be threaded. A proximal end 50b of the actuation rod 60 is connectable to the activation device 16. The proximal end 50b of the actuation rod 50 may comprise a formation 52 that may reside in a corresponding recess in the activation device 16. The formation 62 and corresponding recess in the activation device 16 are configured such that rotation of the activation device 16 results in rotation of the actuation rod 50. For example, the actuation rod formation 52 and a corresponding recess in the activation device 16 may be non-circular cross section so that relative rotation between the activation device 16 and actuation rod 50 is prevented.

Figure 5:
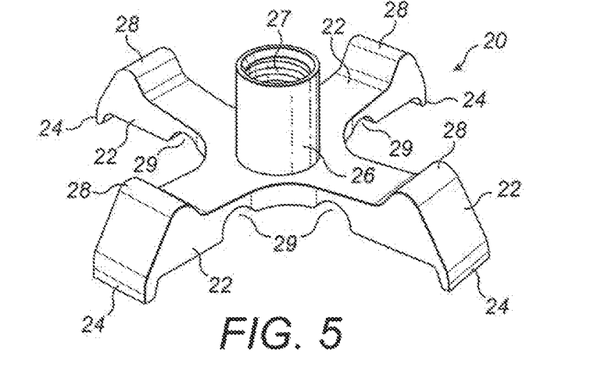
FIG. 5 is a perspective view attachment element according to the example of the present invention.

Referring now to FIG. 5, the attachment element 20 comprises a hub 26 from which the one or more arms 22 extend. The hub 26 comprises an opening 27 for receiving the actuation rod 50. The opening 27 may be threaded for receiving the threaded distal end 50a of the actuation rod 50.

The hub 26 may be provided at the centre of the attachment element 20. The attachment element 20 may be symmetrical and, as shown, the attachment element 20 may possess rotational symmetry about the longitudinal axis of the hub 26. The arms 22 may be equiangularly distributed about the hub 26. Accordingly, with four arms 22 the attachment element may be cross shaped, e.g. cruciform.

The attachment element arms 22 are configured to flex with respect to the hub 26. For example, the arms 22 may bend about an axis that resides in the radial plane. Such a bending axis may be spaced apart from the longitudinal axis.

Figure 6:
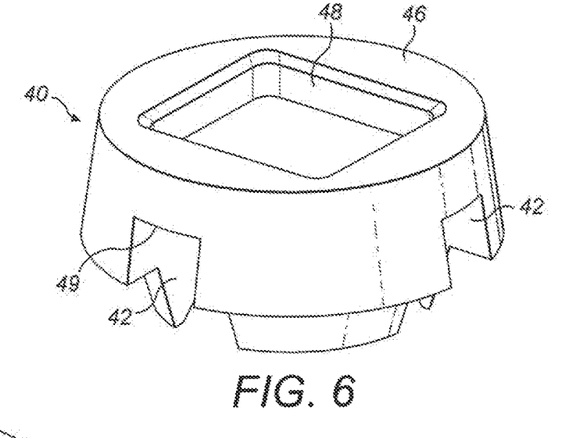
FIG. 6 is a perspective view of an impaction member according the example of the present invention.

Each arm may comprise a pivot surface or edge 28. The pivot surfaces or edges 28 are configured to interact with a corresponding surface or edge 49 of the impaction member 40 (see FIG. 6) so as to form a pivot, fulcrum, about which the engaging portions 24 may rotate when the attachment element moves between the disengaged and engaged positions. The engaging portion 24 and pivot surface or edge 28 may be provided on opposite sides of each arm 22. Furthermore, each arm pivot surface or edge 28 may be provided at a point towards the distal end of the arm 22. However, to aid rotation of the engaging portions 24, the arm pivot surface or edge 28 may be set back from the distal end of the arm. As shown in FIG. 6, the arm pivot surface or edge 28 may comprise a rounded profile, e.g. to facilitate rotation. Alternatively or additionally, the corresponding surface or edge 49 of the impaction member 40 may comprise a rounded profile. The corresponding surface or edge 49 of the impaction ember 40 may otherwise comprise a substantially flat profile.

As depicted in Figure each arm 22 may comprise a reduced thickness portion 29, The reduced thickness portion 29 may aid bending of the arm 22. The reduced thickness portion 29 may be provided between the distal end of the arm and the hub 26 attachment element 20. In particular, the reduced thickness portion 29 may be vided between the pivot surface or edge 28 of the arm 22 and the hub 26 of the attachment element. The reduced thickness portion 29 may be provided on a side of the arm facing away from the impaction member 40, e.g. the side opposite the arm pivot surface or edge 28. The reduced thickness portion 29 may be in the form of a cut-out in the arm 22 and the reduced thickness portion 29 may comprise a curved profile, e.g. to reduce any stress concentrations.

Figure 7:
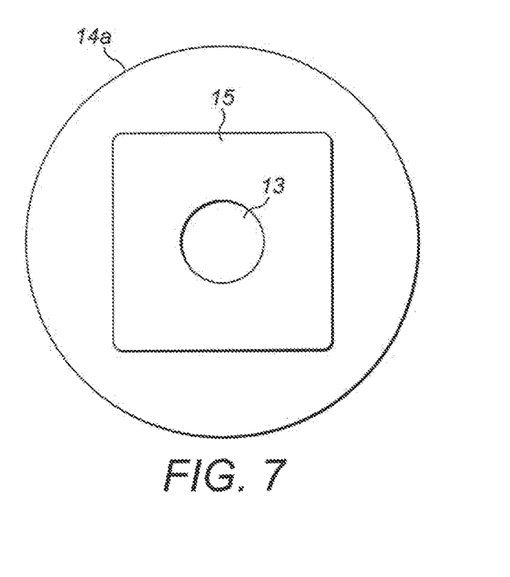
FIG. 7 is an end on view a stem according to the example of present invention.

With reference to FIGS. 6 and 7, an end face 46 of the impaction member 40 is configured to abut against a flange 14a provided at the distal end of the stem 14. A protrusion 15 may be provided on an end face of the flange 14a. As shown, the protrusion 15 may be substantially square shaped, although other non-circular shapes for the protrusion are also envisaged. An opening 13 may be provided in the flange 14a and protrusion 15 for the actuation rod 50 to extend through and into the hollow stem 14. The protrusion 15 may received in a corresponding recess/opening 48 provided in the end face 46 of the impaction member 40. Accordingly, the opening 48 may also be substantially square or any other non-circular shape. The protrusion 15 and opening 48 cooperate such that the impaction member 40 may be constrained from rotating with respect to the stem 14 of the impaction tool 10. The actuation rod 60 and/or attachment element hub 26 may also extend into/through the opening 48.

The operation of the impaction tool 10 according to the present invention will now be described with reference to FIG. 8. FIGS. 8a and 8b show the distal end 10a of the impaction tool 10 before and after engagement with the acetabular cup 2 respectively.

As the impaction tool 10 is brought into engagement with the acetabular cup 2, the centring formations 44 assist in centring the impaction tool 10 with respect to the acetabular cup 2. Once the impaction surface 41 impaction member 40 is in contact with the rim 6 of the acetabular cup, the impaction tool 10 may then be locked to the acetabular cup 2.

The activation device 16 is rotated to move between the disengaged and engaged positions. The actuation rod 50 rotates as a result and the threaded end 50a of the actuation rod rotates in the threaded hob 26. Thus, it will be appreciated that rotation of the activation device 16 and the actuation rod 50 results in linear movement of the attachment element hub 26 thanks to the threaded connection between the hub opening 27 and the actuation rod 50. In other words, as the actuation rod 50 rotates the attachment element hub 26 moves in the axial direction by virtue of the threaded connection between the actuation rod and the attachment element. (The actuation rod 50 may not itself move linearly, although in other examples this may be the case.) As a result the attachment element 20 bends between the disengaged and engaged positions and the impaction tool 10 may grip the rim 6 of the acetabular cup 2. Rotation of the actuation rod 50 may provide a mechanical advantage to bend the attachment element 20. The pitch of the thread at the distal end 50a of actuation rod 50 may be selected to maximise the mechanical advantage. A lock (not shown) may be provided to lock the activation device, actuation rod and/or attachment element into the engaged position.

With the acetabular cup securely attached to the impaction tool, the acetabular cur, may then be manipulated by the operator, e.g. inserted into place. The impaction tool 10 may be impacted and such impact may be transmitted to the acetabular cup 2 via the impaction surface 41. Once the acetabular cup is in place, the attach attachment element 20 may be readily disengaged by rotating the activation device 16 in the opposite direction. The acetabular cup may also be removed from the acetabulum by applying the same process.

Alternatively, the attachment element 20 and actuation rod 50 may be configured such that linear movement of the actuation rod causes the attachment element to bend between the disengaged and engaged positions. The activation device 16 may be threadably connected to actuation rod 50, such that rotation of the activation device causes linear movement of actuation rod and thus bending of attachment element 20.

In other words, the movable threaded connection may be provided at the proximal end 50b of the actuation rod 50 and the actuation rod may be fixed to the attachment element 20 at its distal end 50a. The actuation rod 50 may be rotatably fixed to the attachment element 20, e.g. so that the actuation rod may not rotate with respect to attachment element. For example, the actuation rod 50 and attachment element 20 may be unitary or the actuation rod 50 may be fixed to, the attachment element 20, e.g. by virtue of a weld, locked thread or any other joining means. The actuation rod 60 and attachment element 20 may however be separable. For example, the distal end 50a of the actuation rod 50 may be T-shaped and the T-shaped portion may engage a corresponding recess in the attachment element 20 such that the actuation rod 50 and attachment element 20 rotate together.

As mentioned above, the attachment element 20 and actuation 50 may be configured such that linear movement of the actuation rod causes the attachment element to bend between the disengaged and engaged positions. However, in a further alternative arrangement, linear movement of the actuation rod may be caused without a threaded connection. For example, the activation device may comprise a push button (not shown) which may be connected to the actuation rod 50. Such a push button may be provided at the distal end of the handle 12. The push button may or may not be spring loaded (the resilience of the attachment element may provide a restoring force). Alternatively, the activation device may comprise a lever (not shown). The lever may be pivotably connected to the impaction tool and may be connected, e.g. via a mechanism, to the actuation rod such that rotation of the lever about its pivot point results in linear movement of the actuation rod. The lever may be arranged alongside the handle 12 so that the lever may be squeezed by the same hand holding the handle. The lever may rotate about an axis substantially perpendicular to the longitudinal axis of the actuation rod. The lever may rotate about an axis spaced apart from the longitudinal axis of the actuation rod. The lever may provide a mechanical advantage.

With any of the above examples, one or more limiters (not shown) may be provided prevent the attachment element 20 from being bent beyond a desired threshold. For example, the limiters may limit the movement (rotation and/or linear) of the actuation, rod in the case of a rotating actuation rod, the limiter may be in the form of a torque limiter, e.g. such as found on, a torque wrench. Such a torque limiter may be provided in the rotating activation device 16. The limiters may otherwise comprise features, such as abutment surfaces, configured to limit the movement of the actuation rod, activation device or attachment element. For example, in the case of the lever described above, the lever may be limited to move in a particular range in this way the operator cannot move the actuation rod 50 and thus the attachment element beyond a predetermined amount.

A kit of parts comprising the above-mentioned instrument may be provided. The kit of parts may comprise a range of impaction members and/or a range of attachment elements, which may vary in size. In this way a range of prosthetic implants varying in size may be catered for. The remainder of the impaction tool may otherwise comprise common components and the impaction member and/or attachment element may be interchanged as required.

The present invention provides an instrument for manipulating a prosthetic implant which does not damage the bearing surface of the prosthesis. Furthermore, the instrument requires only a small surface of the prosthesis to grip and therefore has minimal impact on the size of the prosthesis. The instrument of the present invention also does not extend significantly beyond the perimeter of the prosthesis and this is advantageous during surgery where limited space may be available. Any trauma to surrounding tissue may also be reduced.

The instrument of the present invention also requires fewer parts, may be readily dismantled and avoids hinges and associated crevices. This improves the sterilisation of the tool and patient outcomes may be better as a result.

Although described with reference to an acetabular cup, it will be as that the impaction tool the present invention may equally be applied to other prosthetic implants, such a for the shoulder, knee, ankle, elbow etc.

The invention claimed is:

1. An instrument for manipulating a prosthetic implant, the instrument comprising
    an attachment element, operable to engage the implant, wherein the attachment element is bendable between a first position in which the attachment element does not engage the implant and a second position in which the attachment element engages the implant;
    an actuator, the actuator being configured so as to selectively bend the attachment element between the first and second positions upon actuation of the actuator; and
    an impaction member provided at a distal end of the instrument, the impaction member including an impaction surface operable to engage a corresponding surface of the implant,
    wherein the attachment element comprises one or more arms extending from a hub, the arms being configured to flex with respect to the hub,
    wherein the impaction member comprises one or more channels, each channel of the one or more channels being configured to receive a respective arm of the attachment element,
    wherein the attachment element comprises one or more pivot surfaces or edges which are configured to interact with a corresponding surface or edge of the instrument so as to form a pivot about which a portion of the attachment element rotates when the attachment element bends between the first and second positions,
    wherein the actuator comprises an actuation rod, a distal end of which is connected to the attachment element, the actuation rod configured so as to selectively bend the attachment element between the first and second positions upon movement of the actuation rod, and
    wherein the attachment element comprises a threaded opening for receiving a threaded portion of the actuation rod.

2. The instrument of claim 1, wherein the instrument further comprises:
    a stem, the actuation rod being at least partially moveably received within the stem.

3. The instrument of claim 1, wherein the attachment element and actuation rod are configured such that rotation of the actuation rod causes the attachment element to bend between the first position and the second position.

4. The instrument of claim 1, wherein the attachment element and actuation rod are configured such that linear movement of the actuation rod causes the attachment element to bend between the first position and the second position.

5. The instrument of claim 1, wherein the attachment element is constrained from rotating with respect to the remainder of the instrument.

6. The instrument of claim 1, wherein the attachment elements configured to selectively grip a rim of the implant.

7. The instrument of claim 6, wherein the attachment element grips the rim at two or more points on the rim.

8. The instrument of claim 1, herein the attachment element is cross shaped.

9. The instrument of claim 1, wherein each arm comprises the pivot surface or edge.

10. The instrument of claim 9; wherein the arm pivot surface or edge is provided at a point towards a distal end of the arm.

11. The instrument of claim 9, wherein the arm pivot surface or edge is set back from a distal end of the arm.

12. The instrument of claim 1, wherein each arm comprises a reduced thickness portion, the reduced thickness portion being configured to aid bending of the arm.

13. The instrument of claim 1, wherein the impaction member is removably mounted at the distal end of the instrument.

14. The instrument of claim 1, wherein the impaction member comprises one or more centring formations configured to centre the impaction member with respect to the implant.

15. The instrument of claim 1, wherein the corresponding surface or edge of the instrument comprises a corresponding surface or edge of the impaction member.

16. An instrument for manipulating a prosthetic implant, the instrument comprising:
    an attachment element, operable to engage the implant, wherein the attachment element is bendable between a first position in which the attachment element does not engage the implant and a second position in which the attachment element engages the implant, and wherein the attachment element is constrained from rotating with respect to the remainder of the instrument;

an actuator, the actuator being configured so as to selectively bend the attachment element between the first and second positions upon actuation of the actuator; and an impaction member provided at a distal end of the instrument, wherein the attachment element comprises one or more arms extending from a hub; the arms being configured to flex with respect to the hub, wherein the impaction member comprises one or more channels, each channel of the one or more channels being configured to receive a respective arm of the attachment element, wherein the attachment element comprises one or more pivot surfaces or edges which are configured to interact with a corresponding surface or edge of the instrument so as to form a pivot about which a portion of the attachment element rotates when the attachment element bends between the first and second positions;

wherein the actuator comprises an actuation rod, a distal end of which is connected to the attachment element, the actuation rod configured so as to selectively bend the attachment element between the first and second positions upon movement of the actuation rod, and wherein the attachment element comprises a threaded opening for receiving a threaded portion of the actuation rod.

17. An instrument for manipulating a prosthetic implant, the instrument comprising:

an attachment element, operable to engage the implant, wherein the attachment element is bendable between a first position in which the attachment element does not engage the implant and a second position in which the attachment element engages the implant;

an actuator, the actuator being configured so as to selectively bend the attachment ent between the first and second positions upon actuation of the actuator; and an impaction member provided at a distal end of the instrument, wherein the attachment element comprises one or more arms extending from and formed monolithically with a hub, the arms being configured to flex with respect to the hub, each arm comprising a reduced thickness portion configured to aid bending of the arm, wherein the impaction member comprises one or more channels, each channel of the one or more channels being configured to receive a respective arm of the attachment element, and wherein the attachment element comprises one or more pivot surfaces or edges which are configured to interact with a corresponding surface or edge of the instrument so as to form a pivot about which a portion of the attachment element rotates when the attachment element bends between the first and second positions.

18. The instrument of claim 17, wherein the actuator comprises an actuation rod, a distal end of which is connected to the attachment element, the actuation rod configured so as to selectively bend the attachment element between the first and second positions upon movement of the actuation rod.

19. The instrument of claim 18, wherein the attachment element comprises a threaded opening for receiving a threaded portion of the actuation rod.

20. The instrument of claim 17, wherein the one or more arms extend from the hub in a substantially radial plane, and wherein the one or more arms are bendable about an axis that resides in the radial plane.

* * * * *

UNITED STATES PATENT AND TRADEMARK OFFICE
CERTIFICATE OF CORRECTION

PATENT NO. : 10,449,061 B2  
APPLICATION NO. : 15/110505  
DATED : October 22, 2019  
INVENTOR(S) : Slade et al.

Page 1 of 1

It is certified that error appears in the above-identified patent and that said Letters Patent is hereby corrected as shown below:

On the Title Page

Item (56), Column 2, under "Other Publications", Line 1, delete ""Applicattion" and insert --"Application-- therefor In the Claims Column 9, Line 47, in Claim 1, delete "comprising" and insert --comprising:-- therefor Column 10, Line 34, in Claim 6, delete "elements" and insert --element is-- therefor Column 10, Line 37, in Claim 8, delete "herein" and insert --wherein-- therefor

Column 10, Line 41, in Claim 10, delete "claim 9;" and insert --claim 9,-- therefor Column 11, Line 8, in Claim 16, delete "hub;" and insert --hub,-- therefor Column 11, Line 19, in Claim 16, delete "positions;" and insert --positions,-- therefor Column 12, Line 2, in Claim 17, delete "ent" and insert --element-- therefor Signed and Sealed this  
Twenty-sixth Day of May, 2020

Andrei Iancu  
*Director of the United States Patent and Trademark Office*